US008117699B2

(12) United States Patent
Richards et al.

(10) Patent No.: US 8,117,699 B2
(45) Date of Patent: Feb. 21, 2012

(54) SOUND CONDITIONING SYSTEM

(75) Inventors: Sandy M. Richards, Pershing, IN (US); Timothy Joseph Receveur, Guilford, IN (US)

(73) Assignee: Hill-Rom Services, Inc., Batesville, IN (US)

(*) Notice: Subject to any disclaimer, the term of this patent is extended or adjusted under 35 U.S.C. 154(b) by 0 days.

(21) Appl. No.: 12/696,291

(22) Filed: Jan. 29, 2010

(65) Prior Publication Data

US 2011/0185499 A1 Aug. 4, 2011

(51) Int. Cl.
*A61M 21/00* (2006.01)
*A47C 31/00* (2006.01)

(52) U.S. Cl. ................ 5/658; 5/904; 381/301; 381/333; 381/388; 600/28

(58) Field of Classification Search .............. 5/658, 904; 600/27, 28; 381/301, 333, 388
See application file for complete search history.

(56) References Cited

U.S. PATENT DOCUMENTS

| | | | | |
|---|---|---|---|---|
| 3,014,477 | A * | 12/1961 | Carlin | 600/27 |
| 3,660,591 | A * | 5/1972 | Schultz et al. | 174/70 R |
| 4,124,249 | A * | 11/1978 | Abbeloos | 297/217.4 |
| 4,215,241 | A | 7/1980 | Pinkney, Jr. | |
| 4,612,679 | A * | 9/1986 | Mitchell | 5/425 |
| 5,542,138 | A * | 8/1996 | Williams et al. | 5/658 |
| 5,733,320 | A | 3/1998 | Augustine | |
| 5,844,996 | A * | 12/1998 | Enzmann et al. | 381/71.6 |
| 6,658,132 | B1 * | 12/2003 | Moster et al. | 381/388 |
| 6,897,781 | B2 | 5/2005 | Cooper et al. | |
| 7,039,207 | B1 | 5/2006 | Elrod et al. | |
| 7,685,661 | B2 * | 3/2010 | Popilek et al. | 5/639 |
| 7,835,529 | B2 * | 11/2010 | Hernandez et al. | 381/71.2 |
| 7,869,903 | B2 * | 1/2011 | Turner et al. | 700/275 |
| 2007/0104334 | A1 | 5/2007 | Dallam, II et al. | |
| 2008/0243211 | A1 | 10/2008 | Cartwright et al. | |
| 2009/0147969 | A1 | 6/2009 | Kinouchi et al. | |
| 2009/0152917 | A1 | 6/2009 | Ostler et al. | |

FOREIGN PATENT DOCUMENTS

EP 1886707 A1 2/2008

OTHER PUBLICATIONS

European Search Report No. EP 11 15 1970, Dated May 10, 2011, 6 pages.

* cited by examiner

*Primary Examiner* — Michael Trettel
(74) *Attorney, Agent, or Firm* — Barnes & Thornburg LLP

(57) ABSTRACT

A person-support apparatus comprises a frame, a sound generating device, a user interface, and a controller. The sound generating device is configured to generate an audible sound. The user interface is configured to receive an input from a user. The input corresponds to at least one of a sound conditioning system mode and an audible sound adjustment. The controller is electrically coupled to the sound generating device and the user interface. The controller is configured to control the operation of the sound generating device in accordance with the input from the user interface.

21 Claims, 3 Drawing Sheets

SOUND CONDITIONING SYSTEM

BACKGROUND OF THE DISCLOSURE

This disclosure relates generally to person-support apparatuses. More particularly, but not exclusively, one illustrative embodiment relates to a sound conditioning device for a person-support apparatus.

In a hospital room, sounds from different sources, such as, medical equipment, movement of hospital staff and guests, talking, intercoms, etc., can disturb and/or aggravate a person. In some instances the disturbances cause the recovery time to increase by preventing the person from resting comfortably. While various systems have been developed, there is still room for improvement. Thus a need persists for further contributions in this area of technology.

SUMMARY OF THE DISCLOSURE

The present disclosure includes one or more of the features recited in the appended claims and/or the following features which, alone or in any combination, may comprise patentable subject matter.

One illustrative embodiment of the present disclosure can include a person-support apparatus having a sound generating device attached thereon and configured to generate a sound capable of at least one of masking and cancelling an unwanted sound based on the inputs received from a user through a user interface.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
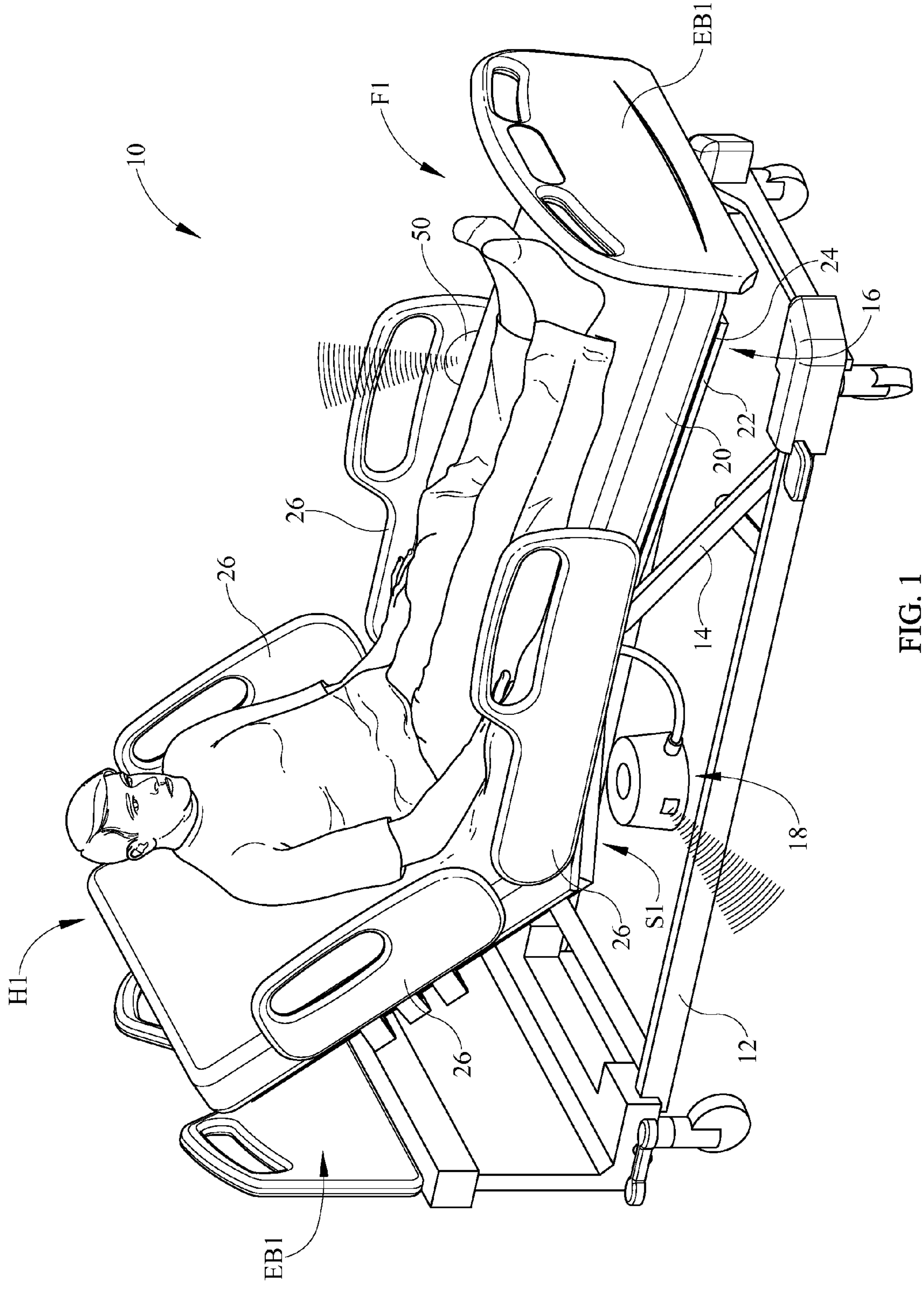
FIG. 1 is a perspective side view of person-support apparatus having a sound generating device attached thereon according to an illustrative embodiment.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment of the present disclosure can include a person-support apparatus having a sound generating device attached thereon and configured to generate a sound capable of at least one of masking and cancelling an unwanted sound based on the inputs received from a user through a user interface.

A person-support apparatus 10 according to one illustrative embodiment of the current disclosure is shown in FIG. 1. The person-support apparatus 10 can be a hospital bed. It should be appreciated that the person-support apparatus 10 can also be a hospital stretcher or an operating table. The person-support apparatus 10 can have a head support section H1 or first section H1, where the head of a person can be positioned, a foot support section F1 or a second section F1, where the feet of the person can be positioned and a seat support section S1 positioned between the head support section H1 and the foot support section F1. The person-support apparatus 10 can include a lower frame 12 or base 12, a plurality of supports 14 coupled with the lower frame 12, and an upper frame 16 supported on the supports 14 above the lower frame 12, and a sound conditioning system 18. It should be appreciated that the supports 14 can be lift mechanisms 14 that can move the upper frame 16 with respect to the lower frame 12. It should also be appreciated that, in one illustrative embodiment, the person-support apparatus 10 can include a person-support surface 20 supported on the upper frame 16.

Figure 2:
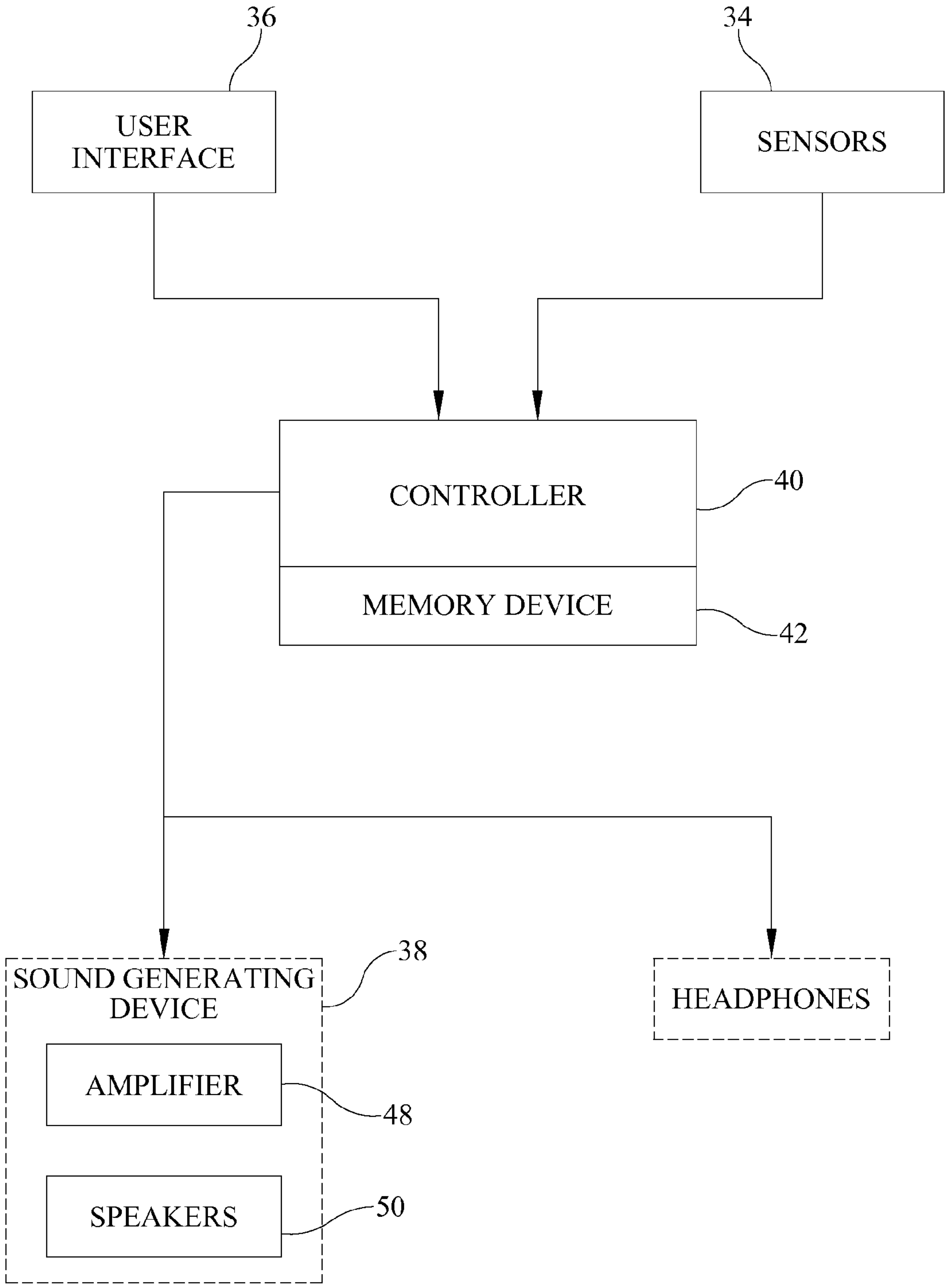
FIG. 2 is a block diagram of a sound control system having the sound generating device described in FIG. 1 according to an illustrative embodiment.
Figure 3:
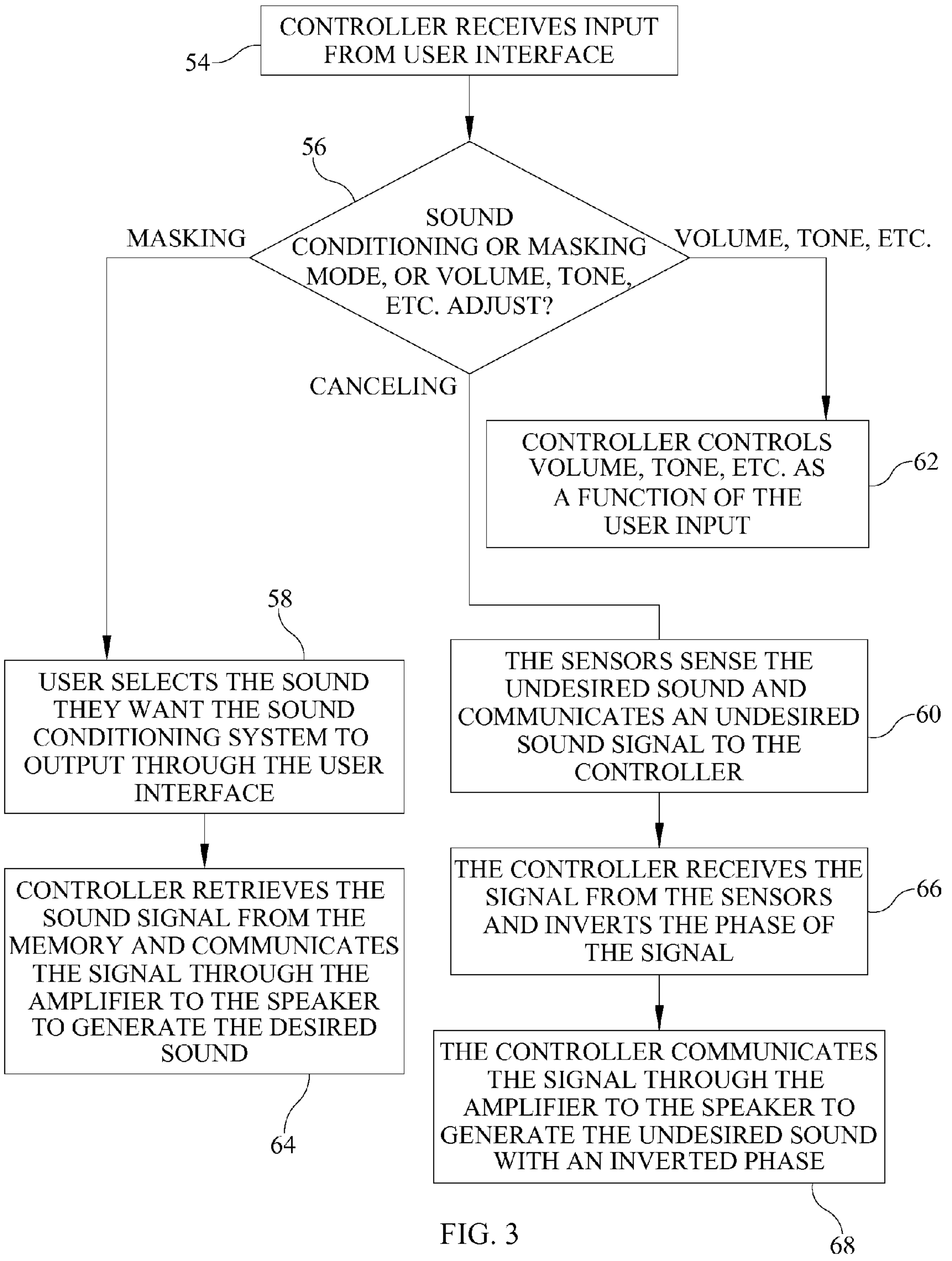
FIG. 3 is a block diagram of the sound control system having the sound generating device described in FIG. 1 according to another illustrative embodiment.

The upper frame 16 can include an intermediate frame 22, a deck 24, siderails 26, and endboards EB1 as shown in FIG. 1. The intermediate frame 22 can be coupled with the supports 14 and can support the deck 24 thereon as shown in FIGS. 1 and 2. The deck 24 can include a head portion 28, a seat portion 30, and a foot portion 32. The head portion 28, the seat portion 30, and the foot portion 32 can be movably coupled with each other and/or the intermediate frame 22.

The sound conditioning system 18 can be coupled to the lower frame 12 as shown in FIG. 1 and can be represented by a block diagram as shown in FIG. 2. It should be appreciated that the sound conditioning system 18 can also be coupled to other portions of the person-support apparatus 10, such as, the endboards EB1 and/or the siderails 26. The sound conditioning system 18 can be configured to reduce or eliminate unwanted sounds. The unwanted sound can be any sound produced within and/or outside the room the person-support apparatus 10 is located in that the person finds unpleasant or upsetting, such as, for example, the operating sound of air conditioners, fans, ECG machines, talking, foot traffic and/or automobile traffic, and/or various other sounds.

The sound conditioning system 18 can reduce or eliminate the unwanted sounds by actively controlling (canceling) and/or masking the unwanted sound. In one illustrative embodiment, the sound conditioning system 18 can mask the unwanted sound by generating a natural or an artificial sound that can be added to the environment to reduce or eliminate a person's awareness of preexisting sounds in a given area. In one illustrative embodiment, the sound conditioning system 18 can generate white noise. In another illustrative embodiment, the sound conditioning system 18 can generate ocean sounds, summer night sounds, rain or storm sounds, rain forest sounds, waterfall sounds, heartbeat sounds, or other sounds. It should be appreciated that masking unwanted sounds can result in enhanced relaxation and/or can sooth the patient to induce sleep.

In another illustrative embodiment, the sound conditioning system 18 can actively control (cancel) the unwanted sound by generating a sound wave with the same amplitude but with inverted phase to the unwanted sound. The combination of the sound wave from the sound generating device and the unwanted sound forms a new sound wave. Since the phase of the sound wave from the sound generating device is inverted compared to phase of the unwanted sound, the sound wave from the sound generating device interferes with that of the unwanted sound and they effectively cancel each other out, i.e, phase cancellation. The resulting sound wave may be so faint as to be inaudible to human ears. It should be appreciated that in some cases the frequency and amplitude of unwanted sounds can be already known, while in other cases the frequency and amplitude of the original sound can be unknown.

The sound conditioning system 18 can include at least one sensor 34, a user interface 36, and a sound generating device 38, and a controller 40. The at least one sensor 34 can be coupled to the upper frame 16 and can be configured to sense ambient sounds. It should be appreciated that the at least one sensor 34 can be coupled to the supports 14, the lower frame 12, the siderails 26, the endboards EB1, on equipment (not shown), or anywhere in the hospital room. In one illustrative embodiment, the at least one sensor 34 is a microphone.

The user interface 36 can be configured to receive inputs from a user corresponding to a desired operation of the sound conditioning system 18. It should be appreciated that the user interface 36 can also be configured to control the functions of the person-support apparatus 10 and/or other equipment present in the room. In one illustrative embodiment, the user interface 36 can be configured to allow a user to activate/deactivate the sound conditioning system 18, select a sound conditioning mode, i.e, masking and/or canceling, and/or the type of sound, volume, tone etc. to be generated by the sound conditioning system 18.

The user interface 36 can be connected to the person-support apparatus 10 via a wired or wireless connection, and/or can be coupled to at least one of the endboards EB1, the siderails 26, a head wall unit (not shown), or other devices or surfaces. The user interface 36 can include a display screen 44 and a plurality of buttons 46. It should be appreciated that the user interface 36 can be a membrane screen interface or touch screen interface. It should also be appreciated that the user interface 36 can include only buttons 46. In one illustrative embodiment, the user interface 36 can be a pendant (not shown). In another illustrative embodiment, the user interface 36 can be a touch screen or membrane screen device, such as, for example, a capacitive touch screen configured to light up only the buttons you should press (as opposed to all of the buttons behind the screen). In yet another illustrative embodiment, the user interface 36 can be integrated into a mattress replacement system (not shown) in an endboard EB1. In still another illustrative embodiment, the user interface 36 can be integrated into a headwall (not shown).

The sound generating device 38 can include an amplifier 48 and a speaker 50. The amplifier 48 can be in communication with the controller 40 and can receive signals from the controller 40 to be output through the speaker 50. The speaker 50 can be electrically coupled to the amplifier 48 and can cooperate with the amplifier 48 to generate an audible output configured to mask and/or cancel the undesirable sounds. In one illustrative embodiment, there can be more than one speaker 50 and the speakers 50 can be positioned symmetrically about the head of the occupant, i.e., the distance from a first speaker 50 to the occupant's first ear is about the same as the distance from a second speaker 50 to the occupant's second ear. In another illustrative embodiment, the speakers 48 can be positioned in the siderails 28. In yet another illustrative embodiment, the speakers 48 can be headphones (not shown) that can connect to the sound conditioning system 18 through a connector (not shown) and/or wirelessly. It should be appreciated that the headphones can also be earphones or earbuds.

The controller 40 can be placed on at least one of the siderails 26, the user interface 36, and/or a mattress replacement system (not shown) in the endboards EB1. The controller 40 can be operatively coupled with the at least one sensor 34, the user interface 36 and the sound generating device 38. The controller 40 can be configured to receive input signals from the at least one sensor 34 and store them in a memory device 42 that can be integrated into the controller 40. The controller 40 can control the sound generating device 38 as a function of the inputs from the at least one sensor 34 in response to inputs from the user interface 36. It should be appreciated that at least one controller 40 can be integrated into the user interface 36 and/or the sound generating device 38. It should also be appreciated that the controller 40 can be in communication with a hospital network (not shown) or nurse call system (not shown) and can receive inputs there from to control operation of the sound conditioning system 18. It should further be appreciated that the controller can be configured to control other functions of the person-support apparatus 10, such as, for example, actuating the lift mechanisms 14 to raise and lower the upper frame 16 with respect to the lower frame 12, articulate portions of the deck 24, monitor the position of a person on the person-support apparatus 10, as well as various other functions.

In one illustrative embodiment, the controller 40 can execute control logic 52 stored in the memory device 42 to control the operation of the sound conditioning system 18. In one illustrative embodiment, the control logic 52 can be illustrated by a flowchart shown in FIG. 4. The control logic 52 can include operations/conditionals 54, 56, 58, 60, 62, 64, 66, 68, and 70. The control logic can begin with operation 54 in which the user interface 36 prompts the user to indicate which mode of operation (i.e., the sound canceling mode and/or the sound masking mode) is desired, and/or whether the volume, tone, etc. of a sound being output by the sound conditioning system 18 should be modified. The user input 36 can generate a user input signal corresponding to the user's input.

In conditional 56, the controller 40 can receive a first input signal from the user interface 36 and determine what mode the user selected and/or whether the volume, tone, etc. of a sound being output by the sound conditioning system 18 should be modified. If the controller 40 determines that the user selected the masking mode, the controller 40 proceeds to operation 58. If the controller 40 determines at the user selected the canceling mode, the controller 40 proceeds to operation 60. If the controller 40 determines at the user indicated that the volume, tone, etc. should be modified, the controller 40 proceeds to operation 62. It should be appreciated that the user can indicate that they want to utilize both the sound masking and canceling features simultaneously.

In operation 58, the user interface 36 prompts the user to indicate what type of sound they would like to use to mask the unwanted sound.

In operation 64, the controller 40 receives the user input signal from the user interface indicating what sound they would like to use to mask the unwanted noise. The controller 40 retrieves the desired sound signal from the memory device 42 and communicates the sound signal through the amplifier 48 to the speaker 50 to generate the audio signal.

In operation 60, the sensors 34 can sense the undesired sound and communicates an undesired sound signal to the controller 40.

In operation 66, the controller 40 can receive the undesired sound signal from the sensors and invert the phase of the undesired sound signal.

In operation 68, the controller 40 can communicate the inverted phase undesired sound signal through the amplifier 48 to the speaker 50 to generate the inverted phase undesired sound, which, when combined with the undesired sound (non-inverted phase), can reduce or effectively eliminate the undesired sound.

In operation 62, the controller 40 can increase/decrease the volume, tone, etc. of an audio signal being generated by the sound conditioning system 18 as a function of the user's input.

Many other embodiments of the present disclosure are also envisioned. For example, a person-support apparatus comprises a frame, a sound generating device, a user interface, and a controller. The sound generating device is configured to generate an audible sound. The user interface is configured to receive an input from a user. The input corresponds to at least one of a sound conditioning system mode and an audible sound adjustment. The controller is electrically coupled to the sound generating device and the user interface. The controller is configured to control the operation of the sound generating device in accordance with the input from the user interface.

In another example, a person-support apparatus comprises a frame, a sound generating device, a user interface and a controller. The sound generating device is positionable on a person's head proximate the person's ears and configured to generate an audible signal. The user interface is configured to receive an input from a user. The controller is operably coupled to the sound generating device and the user interface. The controller is configured to control the operation of the sound generating device in accordance with the input from the user interface.

In yet another example, a person-support apparatus comprises a frame, a sound generating device, a user interface and a controller. The sound generating device is configured to generate an audible signal. The graphical user interface is configured to receive an input from a user. The input corresponds to at least one of a sound conditioning system mode and a audible signal adjustment. The controller is electrically coupled to the sound generating device and the user interface. The controller is configured to control the operation of the sound generating device in accordance with the input from the user interface.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. A person-support apparatus, comprising:

a frame;

a sound detecting sensor, a sound generating device configured to generate an audible sound;

a user interface configured to receive an input from a user, the input corresponding to at least one of a sound conditioning system mode and an audible sound adjustment mode; and a controller electrically coupled to the sound detecting sensor, the sound generating device, and the user interface, wherein when the controller receives an input from the user interface activating the sound conditioning system mode, the controller controls the operation of the sound generating device in accordance with the input from the sound detecting sensor to identify undesirable sound in the region of the person-support apparatus, generate a signal to cancel the undesirable sound, and simultaneously generate a separate masking sound.

2. The person-support apparatus of claim 1, wherein the user interface further includes a sound masking mode where an undesirable sound is masked by a masking sound.

3. The person-support apparatus of claim 2, wherein the masking sound is at least one of white noise and an environmental sound.

4. The person-support apparatus of claim 1, wherein the user interface includes a display.

5. The person-support apparatus of claim 1, wherein the user interface further includes an active sound controlling mode where an undesirable sound is sensed, the phase of the sensed signal is inverted, and the sound generating device outputs the inverted sensed signal to interfere with the undesirable sound.

6. The person-support apparatus of claim 1, wherein the audible sound adjustment mode corresponds to a change in at least one of the volume of the sound output by the sound generating device and the tone of the sound output by the sound generating device.

7. The person-support apparatus of claim 1, wherein the user interface is a pendant.

8. The person-support apparatus of claim 1, wherein the user interface is coupled to a headwall unit.

9. The person-support apparatus of claim 1, further comprising a siderail and an endboard coupled to the frame, the user interface being coupled to at least one of the siderail and the endboard.

10. The person-support apparatus of claim 1, wherein the user interface is coupled to a mattress replacement system.

11. The person-support apparatus of claim 1, wherein the controller is configured to control at least one other function of the person-support apparatus.

12. A person-support apparatus, comprising:

a frame;

a sound detecting sensor, a sound generating device positionable on a person's head proximate the person's ears and configured to generate an audible signal;

a user interface configured to receive an input from a user; and a controller operably coupled to the sound detecting sensor, the sound generating device, and the user interface, wherein when the controller receives an appropriate input from the user interface, the controller controls the operation of the sound generating device in accordance with an input from the sound detecting sensor to identify undesirable sound in the region of the person-support apparatus, generate a signal to cancel the undesirable sound, and simultaneously generate a separate masking sound.

13. The person-support apparatus of claim 12, wherein the sound generating device is an earphone.

14. The person-support apparatus of claim 12, further comprising a siderail and an endboard coupled to the frame, and wherein the sound generating device is a speaker coupled to at least one of the siderail and the endboard.

15. The person-support apparatus of claim 12, further comprising a siderail and an endboard coupled to the frame, the user interface being coupled to at least one of the siderail and the endboard.

16. The person-support apparatus of claim 12, wherein the user interface includes a display.

17. The person-support apparatus of claim 12, wherein the controller is configured to control at least one other function of the person-support apparatus.

18. The person-support apparatus of claim 12, wherein the input from the usercorresponds to at least one of a sound conditioning system mode and an audible sound adjustment, the sound conditioning mode including a sound masking function where an undesirable sound is masked by a masking sound, and an active sound controlling function where an undesirable sound is sensed, the phase of the sensed signal is inverted, and the inverted sensed signal is output by the sound generating device to interfere with the undesirable sound.

19. A person-support apparatus, comprising:

a frame;

a sound detecting sensor, a sound generating device configured to generate an audible signal;

a graphical user interface configured to receive an input from a user, the input corresponding to at least one of a sound conditioning system mode and an audible signal adjustment; and a controller electrically coupled to the sound detecting sensor, the sound generating device, and the user interface, wherein when the controller receives an input from the user interface activating the sound conditioning system mode, the controller controls the operation of the sound generating device in accordance with the input the sound detecting sensor to identify undesirable sound in the region of the person-support apparatus, generate a signal to cancel the undesirable sound, and simultaneously generate a separate masking sound.

20. The person-support apparatus of claim 19, wherein the sound conditioning system mode includes a masking sound and an active sound formed when an undesirable sound signal is sensed, the phase of the sensed signal is inverted, and the inverted sensed signal is output by the sound generating device to interfere with the undesirable sound.

21. The person-support apparatus of claim 19, wherein the controller is configured to control at least one other function of the person-support apparatus.

* * * * *